(12) United States Patent
Hieb et al.

(10) Patent No.: US 9,925,338 B2
(45) Date of Patent: Mar. 27, 2018

(54) APPARATUS AND METHODS FOR FLUID PRESSURIZING UNITS OF INJECTION SYSTEMS

(71) Applicant: ACIST MEDICAL SYSTEMS, INC., Eden Prairie, MN (US)

(72) Inventors: Martin G. Hieb, St. Louis Park, MN (US); David J. Hajicek, Minnetonka, MN (US); Sidney D. Nystrom, Shoreview, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 122 days.

(21) Appl. No.: 15/142,367

(22) Filed: Apr. 29, 2016

(65) Prior Publication Data
US 2016/0243306 A1     Aug. 25, 2016

Related U.S. Application Data

(60) Division of application No. 14/084,256, filed on Nov. 19, 2013, now Pat. No. 9,352,105, which is a
(Continued)

(51) Int. Cl.
*A61M 5/20*      (2006.01)
*A61M 5/315*     (2006.01)
(Continued)

(52) U.S. Cl.
CPC .......... *A61M 5/2053* (2013.01); *A61L 31/048* (2013.01); *A61M 5/007* (2013.01);
(Continued)

(58) Field of Classification Search
CPC .............. A61M 5/007; A61M 5/14546; A61M 5/14566; A61M 5/2053; A61M 5/31511;
(Continued)

(56) References Cited

U.S. PATENT DOCUMENTS 1,165,686 A * 12/1915 McElroy ........... A61M 5/31513
                                                        604/222
1,348,796 A    8/1920 Gronbech
(Continued)

FOREIGN PATENT DOCUMENTS

EP        302248 A1    2/1989
EP        599649 A1    6/1994
(Continued)

OTHER PUBLICATIONS

ACIST CVi Contrast Delivery System User Manual, (P/N 900420-001 Rev. 4), Nov. 2005, 91 pages.
(Continued)

*Primary Examiner* — Quynh-Nhu H Vu
(74) *Attorney, Agent, or Firm* — Fredrikson & Byron, P.A.

(57) ABSTRACT

An injection system includes a syringe, which preferably includes larger and smaller inner diameters, and a plunger. A wiper sidewall of the plunger defines a cavity, into which a plunger shaft of the system is inserted, for moving the plunger, within the syringe, for fluid injection. The plunger includes a feature for engaging the shaft, and the sidewall preferably includes an expandable-contractible portion, in which the feature is formed. When the plunger is initially mounted within the larger inner diameter of the syringe, the portion of the sidewall is expanded and the feature of the plunger does not operably engage the inserted shaft. When the shaft moves the plunger into the smaller inner diameter of the syringe, the portion of the sidewall contracts and the feature operably engages the shaft. A deformable end wall of the plunger may be spaced apart from a distal terminal end of the inserted shaft.

6 Claims, 8 Drawing Sheets

Related U.S. Application Data continuation of application No. 12/324,087, filed on Nov. 26, 2008, now Pat. No. 8,613,730.

(51) Int. Cl.
| | | |
|---|---|---|
| *A61L 31/04* | (2006.01) | |
| *A61M 5/00* | (2006.01) | |
| *A61M 5/145* | (2006.01) | |
| *A61M 5/48* | (2006.01) | |
| *A61M 5/50* | (2006.01) | |

(52) U.S. Cl.
CPC ..... *A61M 5/14546* (2013.01); *A61M 5/31511* (2013.01); *A61M 5/31515* (2013.01); *A61M 5/484* (2013.01); *A61M 5/14566* (2013.01); *A61M 5/31513* (2013.01); *A61M 5/5066* (2013.01); *Y10T 29/49815* (2015.01); *Y10T 29/49826* (2015.01)

(58) Field of Classification Search
CPC .......... A61M 5/31513; A61M 5/31515; A61M 5/484; A61M 5/5066
See application file for complete search history.

(56) References Cited

U.S. PATENT DOCUMENTS

| | | | |
|---|---|---|---|
| 3,147,753 A * | 9/1964 | Nogier | A61M 3/00 604/222 |
| 3,742,949 A | 7/1973 | Hill | |
| 3,874,382 A * | 4/1975 | Nogier | A61M 5/31513 604/222 |
| 3,890,956 A | 6/1975 | Moorehead et al. | |
| 4,215,701 A | 8/1980 | Raitto | |
| 4,266,557 A | 5/1981 | Merry | |
| 4,869,720 A | 9/1989 | Chernack | |
| 4,952,208 A | 8/1990 | Lix | |
| 5,007,904 A | 4/1991 | Densmore et al. | |
| 5,085,638 A | 2/1992 | Farbstein et al. | |
| 5,181,912 A * | 1/1993 | Hammett | A61M 5/5066 604/110 |
| 5,314,416 A | 5/1994 | Lewis | |
| 5,383,858 A | 1/1995 | Reilly et al. | |
| 5,411,489 A | 5/1995 | Pagay et al. | |
| 5,453,093 A | 9/1995 | Haining et al. | |
| 5,620,423 A | 4/1997 | Eykmann et al. | |
| 5,735,825 A | 4/1998 | Stevens et al. | |
| 5,875,976 A | 3/1999 | Nelson et al. | |
| 5,947,929 A * | 9/1999 | Trull | A61M 5/14546 604/131 |
| 6,080,136 A * | 6/2000 | Trull | A61M 5/14546 128/DIG. 1 |
| 6,511,459 B1 | 1/2003 | Fago | |
| 6,752,789 B2 | 6/2004 | Duchon et al. | |
| 7,547,297 B2 | 6/2009 | Brinkhues et al. | |
| 7,797,932 B2 | 9/2010 | Herrick et al. | |
| 8,118,781 B2 * | 2/2012 | Knopper | A61M 5/14566 604/151 |
| 8,551,045 B2 * | 10/2013 | Sie | A61M 5/14566 604/151 |
| 8,613,730 B2 | 12/2013 | Hieb et al. | |
| 2002/0022807 A1 | 2/2002 | Duchon et al. | |
| 2004/0122369 A1 | 6/2004 | Schriver et al. | |
| 2006/0069356 A1 | 3/2006 | Witowski | |
| 2008/0183131 A1 | 7/2008 | Duchon et al. | |
| 2010/0016807 A1 * | 1/2010 | Thilly | A61M 5/31513 604/218 |
| 2010/0042055 A1 * | 2/2010 | Sudo | A61M 5/31513 604/218 |
| 2010/0167231 A1 * | 7/2010 | Dubbe | A61C 5/66 433/80 |

FOREIGN PATENT DOCUMENTS

| | | |
|---|---|---|
| JP | H07313598 A | 12/1995 |
| JP | 2001507963 A | 6/2001 |
| JP | 2001520087 A | 10/2001 |
| JP | 2005511158 A | 4/2005 |
| WO | 9201485 A1 | 2/1992 |
| WO | 9630066 A1 | 10/1996 |
| WO | 9920330 A1 | 4/1999 |
| WO | 9955401 A1 | 11/1999 |
| WO | 02096487 A1 | 12/2002 |
| WO | 2007062315 A2 | 5/2007 |
| WO | 2008134751 A1 | 11/2008 |
| WO | 2010062804 A1 | 6/2010 |
| WO | 2010062807 A1 | 6/2010 |

OTHER PUBLICATIONS

European Patent Application No. 07253965.3, European Search Report dated Feb. 1, 2008, 7 pages.
International Patent Application No. PCT/US2007/080815, International Search Report & Written Opinion dated Mar. 31, 2008, 9 pages.
International Patent Application No. PCT/US2009/064497, International Search Report & Written Opinion dated Feb. 25, 2010, 11 pages.
International Patent Application No. PCT/US2009/064668, International Search Report & Written Opinion dated Mar. 1, 2010, 11 pages.

* cited by examiner

APPARATUS AND METHODS FOR FLUID PRESSURIZING UNITS OF INJECTION SYSTEMS

RELATED APPLICATION

This application is a divisional of U.S. patent application Ser. No. 14/084,256, filed Nov. 19, 2013 and titled APPARATUS AND METHODS FOR FLUID PRESSURIZING UNITS OF INJECTION SYSTEMS, which is a continuation of U.S. patent application Ser. No. 12/324,087, filed Nov. 26, 2008 and titled APPARATUS AND METHODS FOR FLUID PRESSURIZING UNITS OF INJECTION SYSTEMS, the entire contents of which are hereby incorporated by reference herein.

TECHNICAL FIELD

The present disclosure pertains to injection systems and more particularly to apparatus and methods for fluid pressurizing units thereof.

RELATED APPLICATION

This application is a continuation of U.S. patent application Ser. No. 12/324,087, filed Nov. 26, 2008 and titled APPARATUS AND METHODS FOR FLUID PRESSURIZING UNITS OF INJECTION SYSTEMS, the entire contents of which is hereby incorporated by reference herein.

BACKGROUND

Fluid injection systems, which are used to inject a medical fluid into a patient, often include one or more reservoirs, to hold the medical fluid, and one or more pressurizing units, to inject the medical fluid. For example, a contrast media powered injection system may include a reservoir of contrast media coupled to a pressurizing unit, from which contrast is injected, to facilitate imaging during certain medical procedures, such as an angiographic or computed tomography (CT) procedure.

The pressurizing units of medical fluid injection systems typically include at least one syringe and a plunger mounted therein. The plunger is moved, for example, by a motorized plunger shaft of the unit, in a first direction, to draw fluid into the syringe, from the one or more reservoirs, and then, in a second direction, to expel the fluid from the syringe and into the patient, for example, via a catheter, which is coupled to the pressurizing unit. Pressurizing units of many medical fluid injections systems typically employ syringe and plunger subassemblies that are disposable. These disposable syringe and plunger subassemblies may be packaged as a set, wherein the plunger is mounted in the syringe. Once assembled into the pressurizing unit, the syringe and plunger may have an operational life spanning multiple injections, for example, preferably up to 10 or more injections. For those pressurizing units that include a permanent plunger shaft, or ram, assembling the syringe and plunger therein includes coupling the shaft to the plunger prior to an injection; and, removing the syringe and plunger from the pressurizing unit, after one or more injections (for example, for replacement with a new syringe and plunger set), includes decoupling of the shaft from the plunger so that the syringe and plunger may be separated from the shaft.

SUMMARY

Inventive methods and embodiments disclosed herein pertain to a fluid pressurizing unit, for an injection system, that includes a syringe and a plunger mounted therein, wherein the plunger may be operably engaged with a plunger shaft of the unit, yet removable therefrom. Embodiments further pertain to configurations of a syringe and plunger subassembly, for the fluid pressurizing unit, and to configurations of an individual plunger suited for incorporation in the fluid pressurizing unit.

According to some embodiments, the plunger includes a wiper sidewall, which has a radially expandable-contractible portion, extending in proximity to a proximal end of the plunger, and a mating feature, which is formed in the expandable-contractible portion and projects into a cavity of the plunger, which cavity is surrounded by the wiper sidewall and has an opening at the proximal end of the plunger. When the plunger, according to these embodiments, is initially mounted within the syringe, such that the expandable-contractible portion is located within a first length of the syringe, the expandable-contractible portion is expanded, so that the mating feature of the plunger is not operably engaged with an engaging feature of the plunger shaft, which is approximately aligned therewith. According to some methods, a terminal portion of the plunger shaft is initially inserted into the cavity, when the plunger is located within the first length of the syringe, at which point the engaging feature of the shaft may be approximately aligned with the mating feature of the plunger. When the plunger shaft is subsequently advanced, to move the plunger, of these embodiments, into a second length of the syringe, wherein an inner diameter of the syringe is smaller than that of the first length, the expandable-contractible portion is contracted so that the mating feature of the plunger is operably engaged with the engaging feature of the plunger shaft.

According to some additional embodiments, the wiper sidewall of the plunger includes an external sealing lip located in proximity to a distal end of the plunger, and the plunger further includes a deformable distal end wall. The wiper sidewall and the deformable distal end wall define the cavity of the plunger, and the terminal portion of the plunger shaft is of a size and shape so that an a gap exists between a terminal end of the terminal portion and the deformable distal end wall of the plunger, when the shaft is fully inserted into the cavity thereof. The wiper sidewall, of these additional embodiments, may, or may not, include the deformable portion, as described above.

Some additional methods of the present disclosure include those directed toward disabling the syringe and plunger subassembly, for removal of the subassembly from the pressurizing unit. According to these methods, the plunger disengages from the plunger shaft of the unit, as the plunger shaft is retracted from a first position, within the syringe, to a second position, within the syringe, and, then, the plunger is allowed to be drawn back toward the first position, prior to removing the subassembly from the pressurizing unit.

BRIEF DESCRIPTION OF THE DRAWINGS

The following drawings are illustrative of particular methods and embodiments of the present disclosure and, therefore, do not limit the scope of the invention. The drawings are not to scale (unless so stated) and are intended for use in conjunction with the explanations in the following detailed description. Methods and embodiments will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary methods and embodiments. Examples of constructions, materials and dimensions are provided for selected elements, and all other elements employ that which is known to those of skill in the field of the invention. Those skilled in the art will recognize that many of the examples provided have suitable alternatives that can be utilized.

Figure 1:
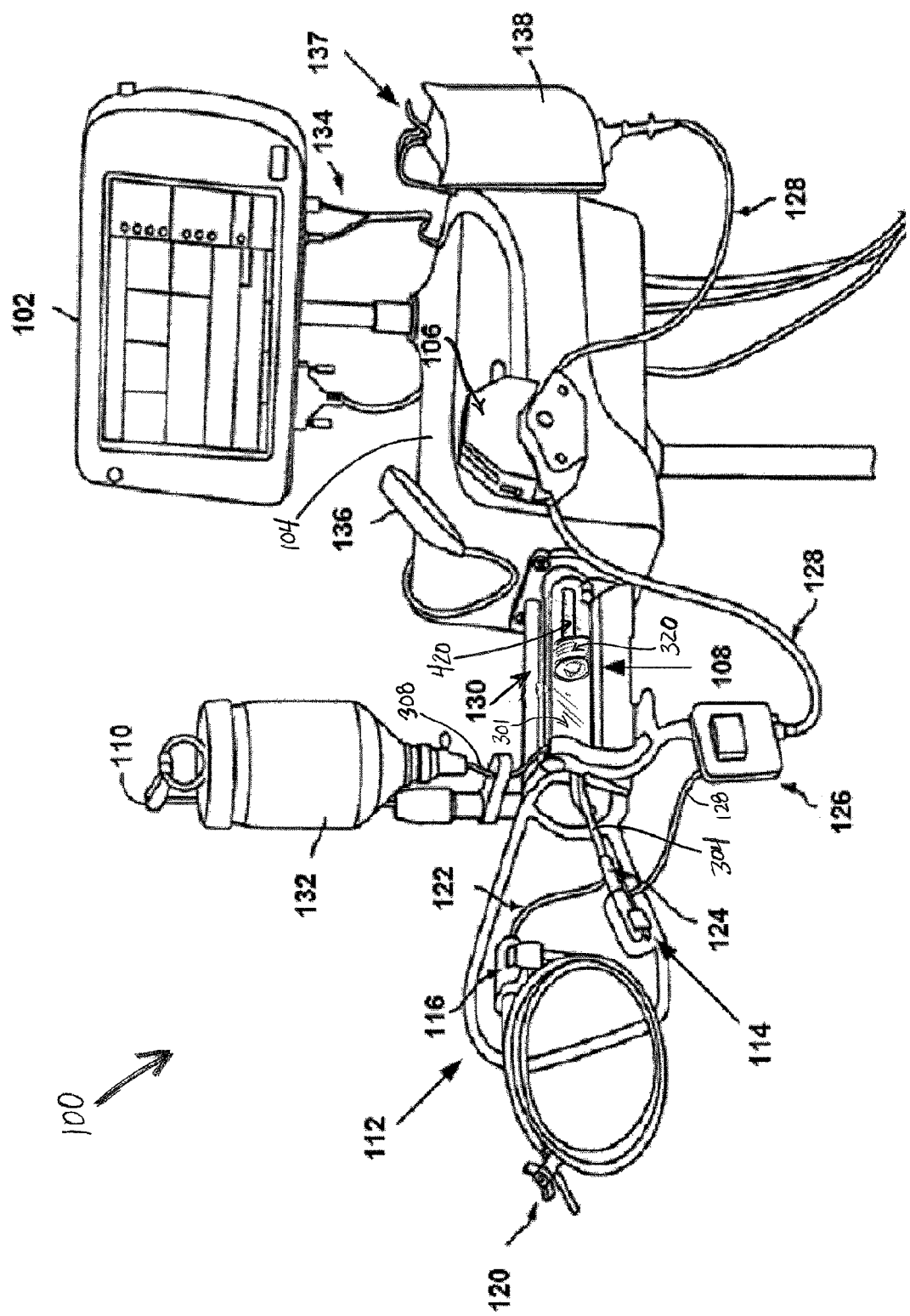
FIG. 1 is a perspective view of a fluid injection system, which may incorporate embodiments of the present invention.

FIG. 1 is a perspective view of a fluid injection system 100, which may incorporate embodiments of the present invention. FIG. 1 illustrates system 100 including, a fluid pressurizing unit 130 mounted in a sleeve 108, that extends from an injector head 104 of system 100, and a first fluid reservoir 132. Reservoir 132 is shown hanging from a holder 110 and being coupled to pressurizing unit 130, via an input tubing line 308, in order to supply fluid, for example, a contrast agent, to unit 130. Fluid pressurizing unit 130 is shown including a syringe 301, in which a plunger shaft 420 extends, and a plunger 320, which is mounted in syringe 301 and coupled to a plunger shaft 420.

According to the illustrated embodiment, shaft 420 is coupled to a motor assembly, which is contained in injector head 104 and which actuates shaft 420 to drive plunger 320 in reciprocating directions within syringe 130. Injector head 104 may include a programmable controller to drive the motor assembly. The controller preferably includes a digital computer, which may be programmed, for example, via a control panel 102 of system 100. The controller may further include a motor drive circuit, amplifier, tachometer, potentiometer, rectifier, pressure sensing load cell and A/D converter, for example, as described in column 10, line 45—column 11, line 2 of commonly-assigned U.S. Pat. No. 6,752,789, which passage is hereby incorporated by reference. When shaft 420 is actuated to move plunger 320 proximally, toward injector head 104, in a suction stroke, fluid, from reservoir 132, is drawn into syringe 301, via input line 308, and, when shaft 420 moves plunger 320 distally, in a compression stroke, the fluid is expelled out from syringe 301, through an output tubing line 304. FIG. 1 further illustrates output tubing line 304 coupled to a tubing line 122, which is mounted on a module 112 of system 100; tubing line 122 may be connected to a patient line, via a connector 120, so that the fluid, which is expelled from syringe 301, is injected into a patient, for example, to facilitate imaging.

With further reference to FIG. 1, system 100 includes a second fluid reservoir 138, which hangs from a hook 137 and from which fluid, for example, a diluent, such as saline, is drawn by a peristaltic pump 106, through a tubing line 128; pump 106 is shown mounted on injector head 104. System 100 further includes a manifold sensor 114 and a manifold valve 124, for controlling the flow of fluids into tubing line 122, either from tubing line 128, or from pressurizing unit 130, via tubing line 304. Manifold valve 124 may comprise a spring-biased spool valve, or another type of valve, for example, a check valve. Manifold sensor 114 can detect the position of manifold valve 124 and report this position to injector head 104.

A pressure transducer 126 is shown coupled to tubing 128; when tubing 122 is connected to a patient line, that extends within a patient, pressure transducer 126 is capable of functioning as a hemodynamic monitor for the patient. Pressure transducer 126 converts detected pressures into electrical signals that may be monitored or otherwise used by system 100 or another monitoring device. An air bubble detector 116 is shown coupled to tubing line 122. Detector 116 is capable of generating an alarm signal, upon detection of a measurable, or otherwise significant, amount of air within tubing line 122. In addition, device 100 may automatically pause, or terminate, a fluid injection procedure, when detector 116 detects air in the tubing.

An operator of system 100, such as a clinician, may use control panel 102 of system 100 to set up various parameters and/or protocols to be used for a given injection procedure. The operator may interact with control panel 102, for example, via a touch-screen panel, to enter injection parameters for flow rate, maximum injection volume, maximum injection pressure, rise time, or other parameters. Control panel 102 may further display operating parameters of system 100 to the operator, and/or warning or alarm messages, for example, indicating that air has been detected by air bubble detector 116.

FIG. 1 also shows a hand-control device 136 coupled to control panel 102, via a connector 134, which may be connected to, or disconnected from, control panel 102. An operator may manipulate hand-control device 136 to control injection of fluid from system 100. For example, the operator may use hand-control device 136 as a variable-rate control device to variably control the rate of flow of fluid from system 100 (e.g., flow of fluid out of pressurizing unit 130). Hand-control device 136 may comprise an electrical device or a pneumatic device.

Because system 100 may deliver many injections over a number of patient procedures, injection fluids may need to be continuously replaced. Injector head 104 may automatically replenish fluid to syringe 301, for example, based upon monitoring of injection volumes therefrom and comparing to an initial, input, volume; or the operator of system 100 may need to manually initiate a fluid replenishment procedure, upon detection that a fluid volume within syringe 301 has been depleted to a critical volume. It should be noted that injector head 104 may automatically replenish fluid to syringe 301 based upon operational state information, other than injection volumes. For example, if injector head 104 determines that system 100 is currently delivering fluid from pump 106, but not from syringe 301, and that syringe 301 is not filled to capacity, injector head 104 may cause the motor assembly to actuate plunger shaft 420 in order to draw additional fluid into syringe 301, via input line 308.

Figure 2:
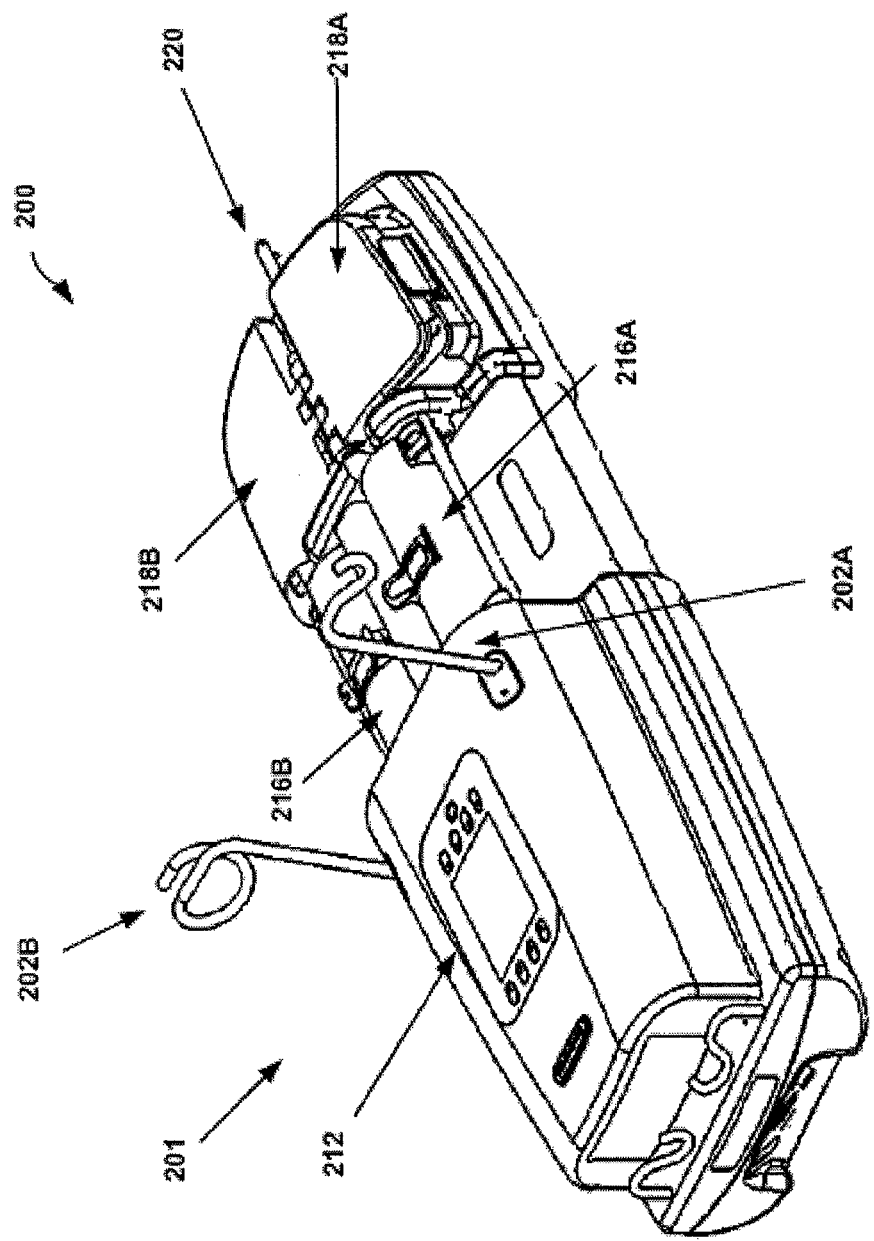
FIG. 2 is a perspective view of an alternative fluid injection system, which may also incorporate embodiments of the present invention.

Turning now to FIG. 2, an alternative fluid injection system 200 is shown in perspective view. Like system 100, system 200 may incorporate embodiments of the present invention. FIG. 2 illustrates system 200 including a control panel 212, which is mounted on an injector head 201 of system 200, and first and second sleeves 216A, 216B, which each extend between injector head 201 and a corresponding one of first and second front end assemblies 218A, 218B of system 200. FIG. 2 further illustrates system 200 including first and second reservoir holders 202A, 202B, and, although not shown, it should be appreciated that a reservoir mounted on each of holders 202A, 202B supplies a fluid to a corresponding fluid pressurizing unit, which is contained in the corresponding sleeve 216A, 216B.

Each fluid pressurizing unit of system 200 may be very similar to unit 130 of system 100 and include a syringe, which is mounted in one of sleeves 216A, 216B, a plunger, which is mounted in the syringe, and a plunger shaft, which extends from injector head 201, into the syringe, and is coupled to the plunger. Furthermore, like system 100, a motor assembly may be coupled each of the plunger shafts, to actuate each shaft, independently, in order to drive the corresponding plunger in reciprocating directions, for alternating suction and compression strokes. The motor assemblies are contained within injector head 201 and may be controlled and monitored by one or more processors of a programmable controller, also included in head 201. It should be understood that first and second front end assemblies 218A, 218B, of system 200, contain input and output tubing lines for each pressurizing unit, wherein each input tubing line supplies fluid from the corresponding reservoir to the corresponding syringe, and each output tubing line carries fluid expelled from the corresponding syringe to a patient line, via a manifold valve. FIG. 2 illustrates a guide rod 220, which facilitates connection of the patient line to system 200. One of the pressurizing units of system 200 may expel a contrast agent for injection into the patient, via the connected patient line, and the other pressurizing unit, a diluent, such as saline. Valves and sensors, similar to those described above for system 100, may be incorporated into the tubing lines of system 200, which are contained within front end assemblies 218A, 218B, in order to facilitate the operation of system 200.

Figure 3A:
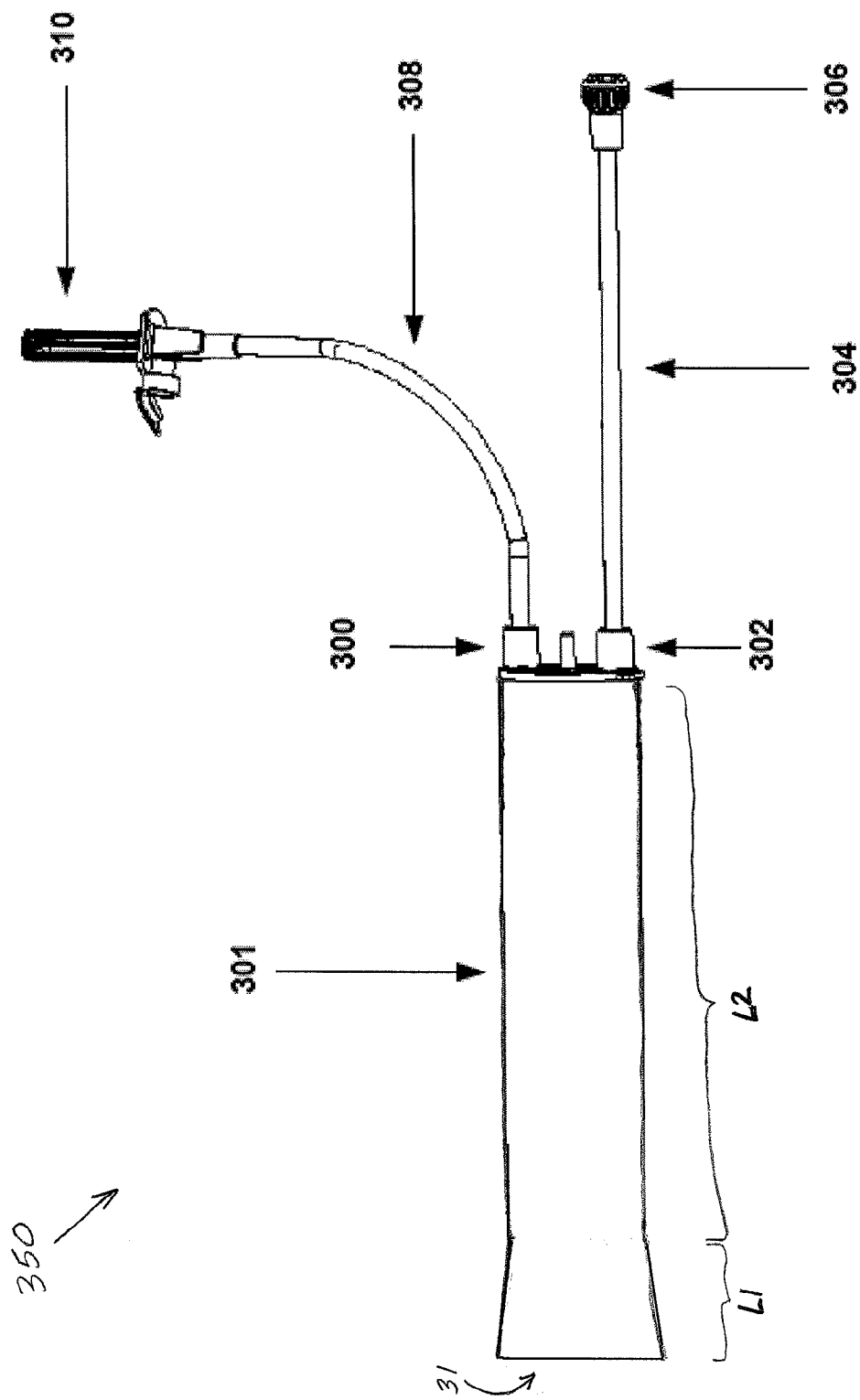
FIG. 3A is a plan view of a subassembly for a fluid pressurizing unit, according to some embodiments of the present invention.

FIG. 3A is a plan view of a subassembly 350 for a fluid pressurizing unit, such as for unit 130, shown in FIG. 1, according to some embodiments of the present invention. It should be noted that subassembly 350 may also be employed by one or both of the pressurizing units of system 200. FIG. 3A illustrates subassembly 350 including syringe 301, input tubing line 308 and output tubing line 304. FIG. 3A further illustrates syringe 301 including a first distal port 300, to which input tubing line 308 is coupled, a second distal port 302, to which output tubing line 304 is coupled, and a proximal opening 31. With reference to FIG. 3B, which is a perspective view looking into proximal opening 31 of syringe 301, plunger 320 may be seen mounted within proximal opening 31, such that an opening 312 into a cavity 321 of plunger 320 faces proximally, for coupling with plunger shaft 420 (FIG. 1), when subassembly 350 is assembled into unit 130, for example, as is illustrated in the section view of FIG. 4A. Subassembly 350 may be provided as a disposable subassembly, packaged as a set, which is replaced with a new set after a given number of injections.

Figure 3C:
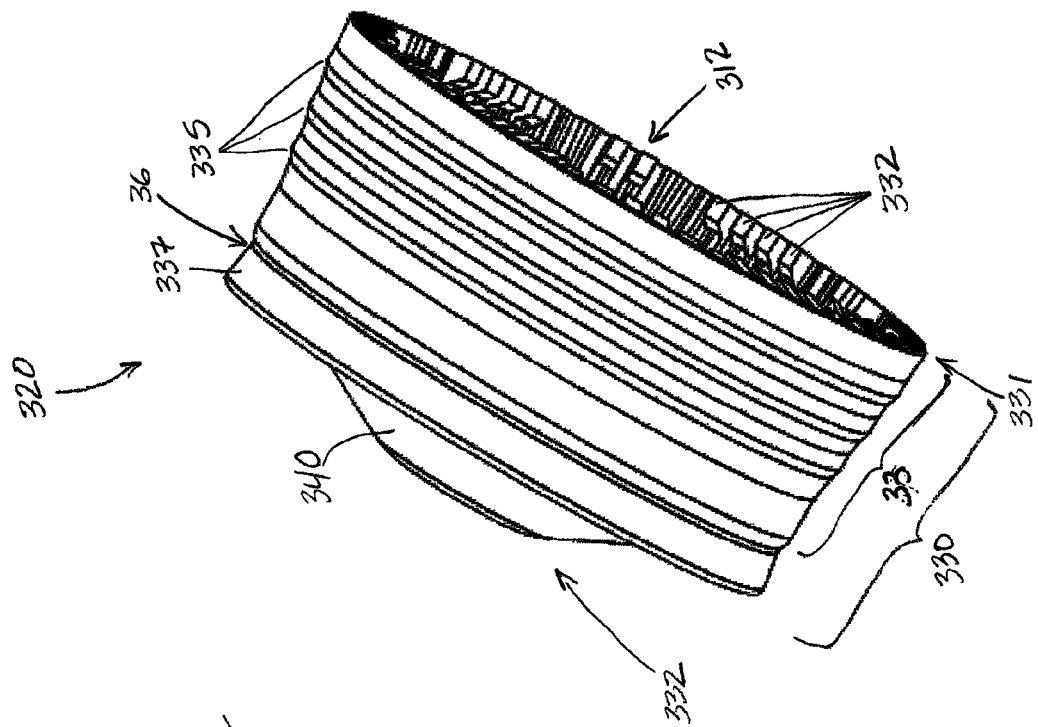
FIG. 3C is a perspective view of a plunger, separated from the subassembly of FIGS. 3A-B, according to some embodiments.
Figure 3B:
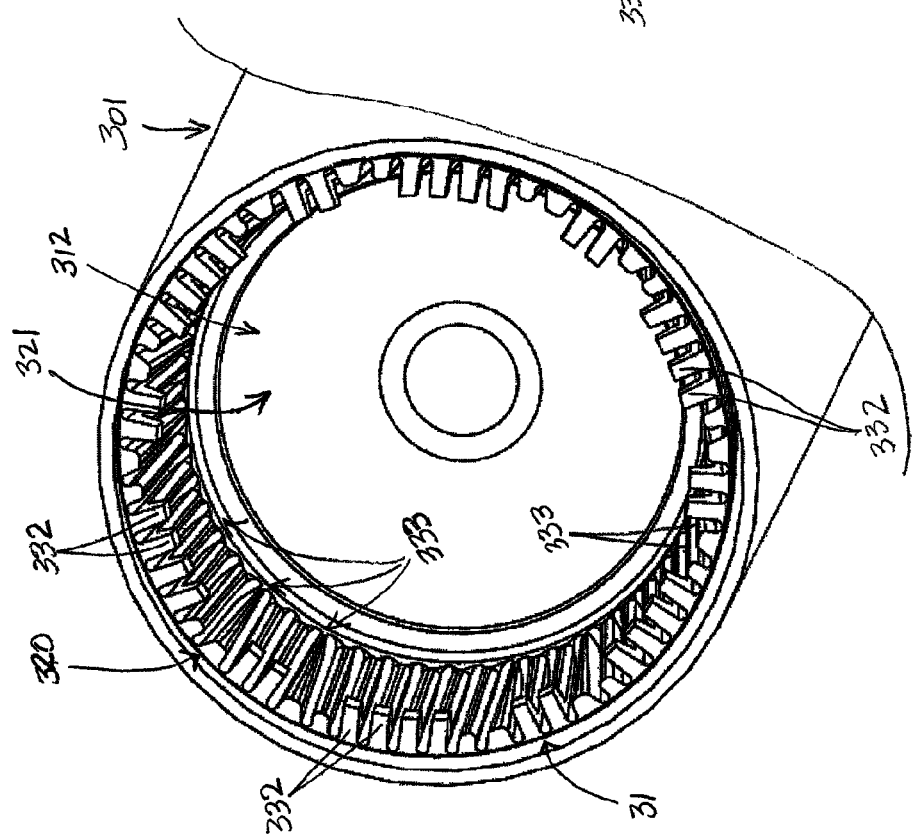
FIG. 3B is a perspective view of a portion of the subassembly, shown in FIG. 3A, according to some embodiments.

FIG. 3C is a perspective view of plunger 320, separated from subassembly 350, according to some embodiments. FIG. 3C illustrates plunger 320 including an optional distal end wall 340 and a wiper sidewall 330, which extends between a proximal end 331 and a distal end 332 of plunger 320, for sealing with an inner surface 311 (FIGS. 4A-B) of syringe 301, during suction and compression strokes of plunger 320, for example, as driven by shaft 420. According to the illustrated embodiment, in order to facilitate the sealing with inner surface 311, wiper sidewall 330 includes a plurality of external sealing ridges 335 and an external sealing lip 337, which will be described in greater detail, below.

FIG. 3C further illustrates wiper sidewall 330 extending proximally, from end wall 340 to opening 312 of cavity 321, and including a radially expandable-contractible portion 33, which surrounds opening 312. FIGS. 3B-C illustrate a plurality of longitudinally extending ribs 333 being formed in an inner surface of wiper sidewall 330, extending distally from proximal end 331 of plunger 320, and being spaced apart from one another about a circumference of cavity 321.

According to the illustrated embodiment, ribs 333 facilitate the expandable and contractible nature of radially expandable-contractible portion 33 of wiper sidewall 330, without sacrificing a structural integrity thereof for sealing. FIGS. 3B-C further illustrate a plurality of tabs 332, each of which are formed on a number of ribs 333, in proximity to proximal end 331 of plunger 320, and project into cavity 321, as a mating feature for operably engaging with an engaging feature of plunger shaft 420.

According to some preferred embodiments, plunger 320 is a single, injection molded component, such that all of the above-described features, which are shown in FIGS. 3B-C, are integrally formed. Plunger 320 is preferably formed from a relatively soft and flexible thermoplastic material, such as polyethylene or polypropylene. The material forming plunger 320 may, for example, have a density of approximately 0.955 g/cm3. According to an exemplary embodiment, plunger 320 is formed, for example, molded, from a high density polyethylene (HDPE), such as Dow HDPE 25455, manufactured by Dow Chemical Company, Midland Mich. A lubricant may be applied over an external surface of wiper sidewall 330, in order to reduce friction at the interface between sidewall 330 and inner surface 311 of syringe 301, which friction could cause plunger 320 to seize within syringe 301, for example, via heat welding, in extreme cases. According to some preferred methods, the lubricant, for example, a silicone-based and biocompatible lubricant, is applied in an annular recess 36 of wiper sidewall 330, prior to mounting plunger 320 within syringe 301, such that, when plunger 320 is moved distally within syringe 301, the lubricant spreads proximally along the interface between wiper sidewall 330 and inner surface 311 of syringe 301. A dynamic viscosity of the lubricant may be between approximately 1,000 centipoise (cP) and approximately 500,000 cP, preferably approximately 100,000 cP.

Figure 4A:
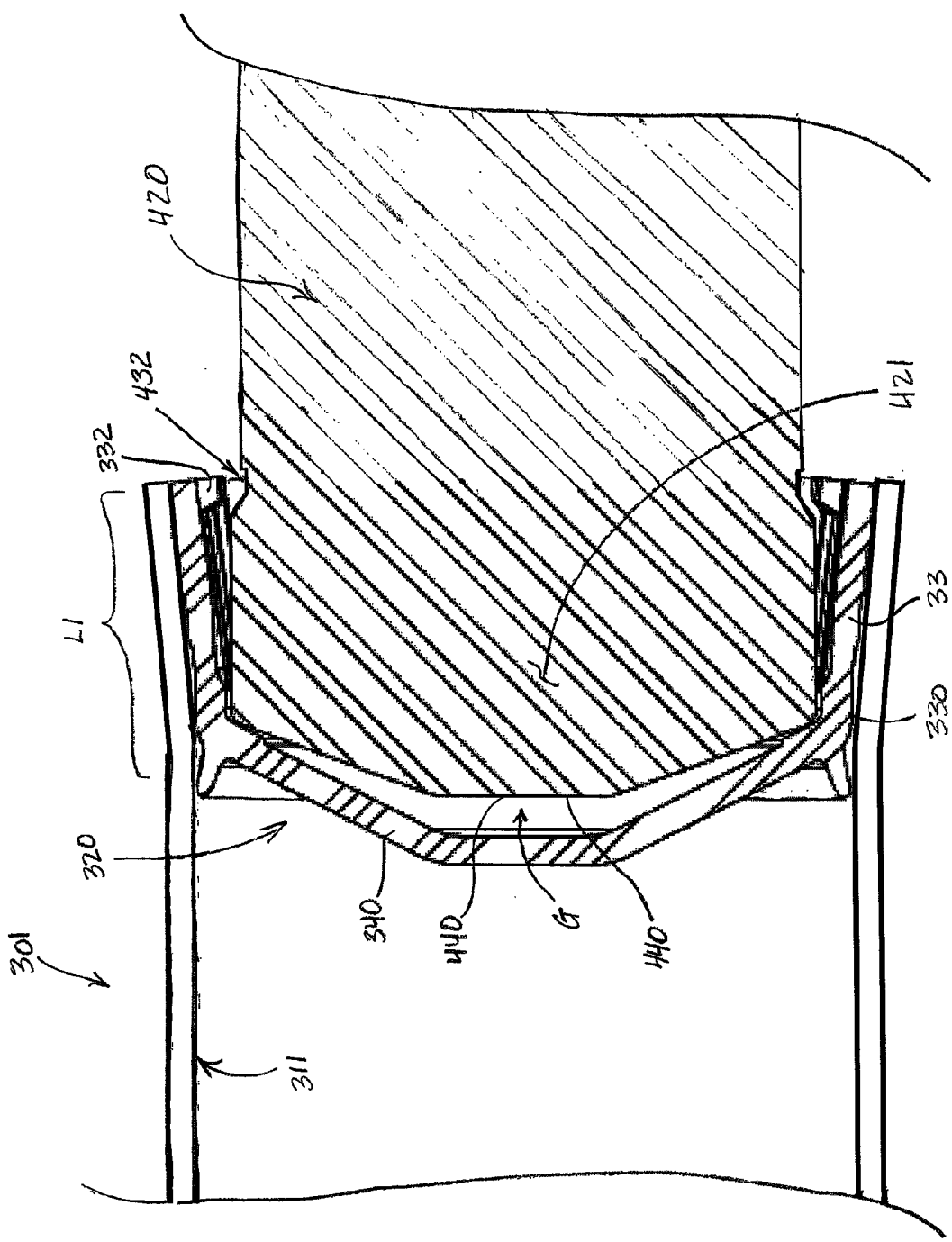
FIG. 4A is a cross-section view of a portion of a fluid pressurizing unit, in a first condition, according to some embodiments.
Figure 4B:
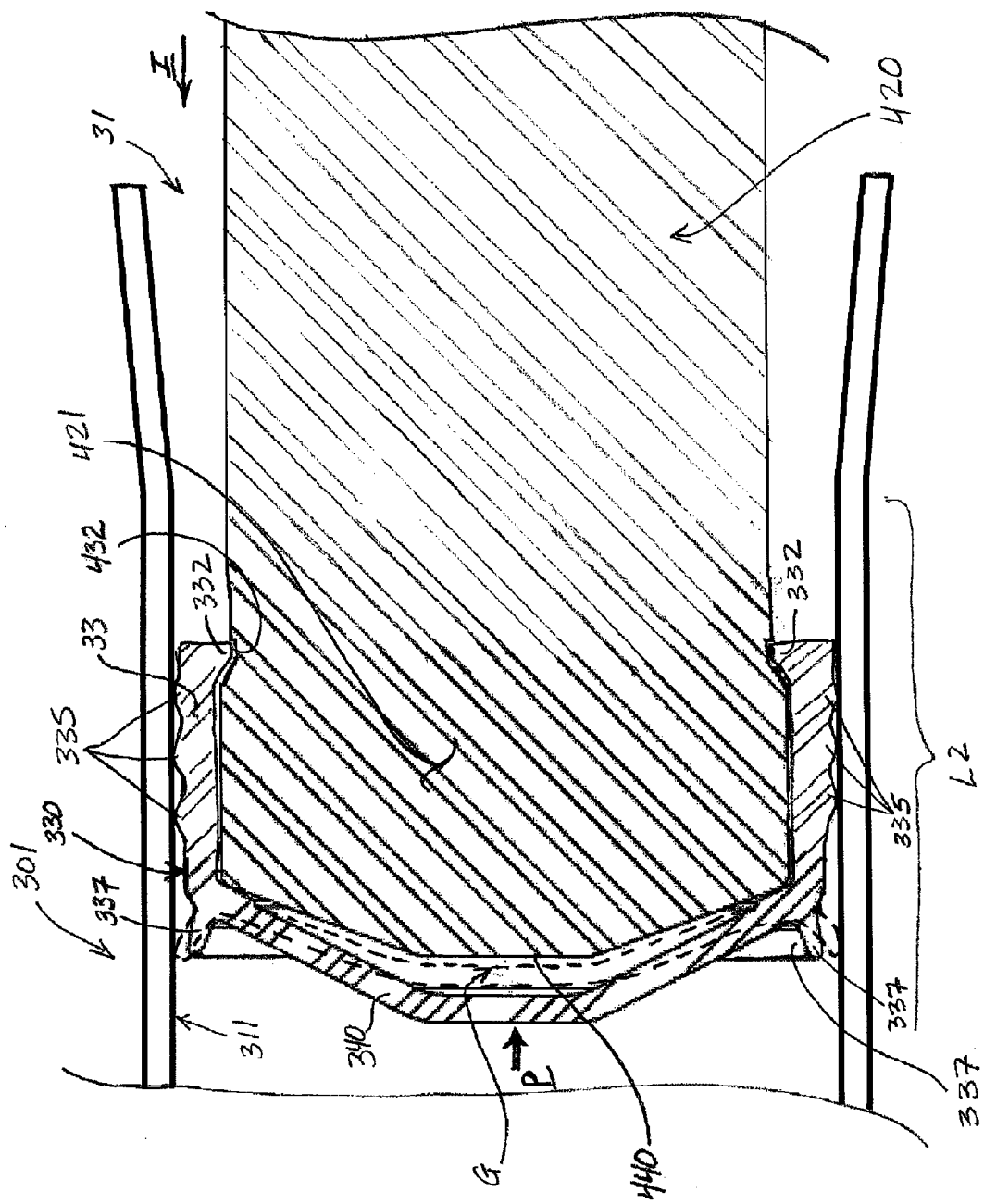
FIG. 4B is a cross-section view of the portion of the unit, shown in FIG. 4A, in a second condition, according to some embodiments.

With reference back to FIG. 3A, syringe 301 is shown including a first length L1 and a second length L2, wherein first length L1 extends from proximal opening 31 to second length L2. Turning now to FIGS. 4A-B, which are cross-section views of a portion of a fluid pressurizing unit that includes subassembly 350, for example, unit 130 of FIG. 1, a significance of lengths L1 and L2, in conjunction with expandable-contractible portion 33 of plunger 320, will be described. FIGS. 4A-B show a portion of inner surface 311 of syringe 301, that extends over first length L1, defining a first inner diameter of syringe 301, and another portion of inner surface 311, that extends over second length L2, defining a second inner diameter of syringe 301, which is less than the first inner diameter. FIG. 4A illustrates a terminal portion 421 of plunger shaft 420 having been inserted into proximal opening 31 of syringe 301 and into cavity 321 (FIG. 3B) of plunger 320, which is initially mounted within proximal opening 31. FIG. 4A further illustrates shaft 420 including an engaging feature, that is formed by a groove 432 and is located at a proximal end of terminal portion 421 of shaft 420. According to the illustrated embodiment, the first diameter of syringe 301 allows expandable-contractible portion 33 of wiper sidewall 330 to be in a relaxed, or expanded state, so that terminal portion 421 of plunger shaft 420, upon initial assembly, may be freely inserted into cavity 321, without operably engaging the mating feature, for example, tabs 332, of plunger 320 within groove 432. FIG. 4B illustrates the inserted terminal portion 421 of plunger shaft 420 having been advanced distally, per arrow I, within syringe 301, until wiper sidewall 330 of plunger 320 is contained within second length L2. Within the smaller inner diameter of second length L2, expandable-contractible portion 33 of wiper sidewall 330 is contracted, so that tabs 332 of plunger 320 are now operably engaged within groove 432 of plunger shaft 420.

FIGS. 4A-B further illustrate terminal portion 421 of plunger shaft 420 having a size and shape to fully support wiper sidewall 330, for sealing engagement with inner surface 311 of syringe 301, when terminal portion 421 is fully inserted into cavity 321 of plunger 320. Yet, the size and shape of terminal portion 421 allow for a gap G to exist between end wall 340 of plunger 320 and a distal terminal end 440 of fully inserted terminal portion 421. According to some preferred embodiments of the present invention, end wall 340 of plunger 320 is deformable, so that, at a given threshold pressure, for example, directed per arrow P of FIG. 4B, during a compression stroke of plunger shaft 420, end wall 340 deforms into gap G, for example, per the dashed lines of FIG. 4B. This deformation of end wall 340 forces sealing lip 337 radially outward and into tighter sealing engagement with inner surface 311 of syringe 301. During suction strokes of plunger shaft 420, and during those compression strokes wherein pressures are lower than the threshold pressure, sealing ridges 335 of wiper sidewall 330 can maintain adequate sealing engagement with inner surface 311, to prevent fluid from leaking past plunger 320, without relying on sealing lip 337. Although a particular number and form of sealing ridges 335 are illustrated, embodiments of the invention are not so limited, and any form and/or number of suitable sealing ridges, known to those skilled in the art, may be employed by plunger 320.

According to an exemplary embodiment, the threshold pressure for deformation of end wall 340, during a compression stroke, may range from approximately 50 psi to approximately 200 psi. It should be noted, however, that some deformation of end wall 340 begins at an even lower pressure, continuing on up to the higher pressures, to provide a tighter seal as the pressure increases. For example, it was found, during testing, that a sealing lip of a plunger, for example, similar to plunger 320, deflected, radially outward, up to 0.025 inch, when not constrained by a syringe; such deflection would provide robust sealing during the compression stroke of the plunger shaft 420, in high pressure applications, of the pressurizing unit. During those compression strokes of plunger shaft 420 that expel a contrast agent from syringe 301, as previously described, pressures may reach or exceed approximately 1200 psi, during certain types of injection procedures, for example, angiography imaging procedures. It should be noted that the radial expansion of sealing lip 337, which is allowed by gap G, in conjunction with a deformable nature of end wall 340, can also make up for a compression set of wiper sidewall 330, which could occur if plunger 320 is 'parked' for a period of time within syringe 301. The radial expansion of sealing lip 337 may also make up for dimensional variability, that may be encountered in manufacturing relatively large volumes of plunger and/or syringe components, and/or may result from aging and/or gamma sterilization, particularly of the plunger components.

The initial position of plunger 320, within first length L1 of syringe, for example as shown in FIGS. 3B and 4A, can prevent plunger 320 from taking a compression set during the time, prior to use, in which subassembly 350 (FIG. 3A) remains in storage. Once subassembly 350 is assembled into a fluid pressurizing unit of an injection system, for example unit 130 of system 100, the operable engagement between plunger 320 and plunger shaft 420, for example, as illustrated in FIG. 4B, enables plunger shaft 420 to move plunger 320 within second length L2 of syringe 301 over multiple reciprocating compression and suction strokes, while wiper sidewall 330 of plunger 320 remains in sealing engagement with inner surface 311 of syringe.

To separate subassembly 350 from plunger shaft 420, for example, after a certain number of injections, terminal portion 421 of shaft 420 may be retracted back into first length L1 of syringe 301, where expandable-contractible portion 33 of plunger 320 may expand, as shown in FIG. 4A, so that plunger 320 may be readily separated from shaft 420. Separation of plunger 320 from shaft 420 may be desired in order to install a new subassembly, that includes a new plunger mounted in a syringe, and/or to assure that plunger 320 is not re-used.

Figure 5:
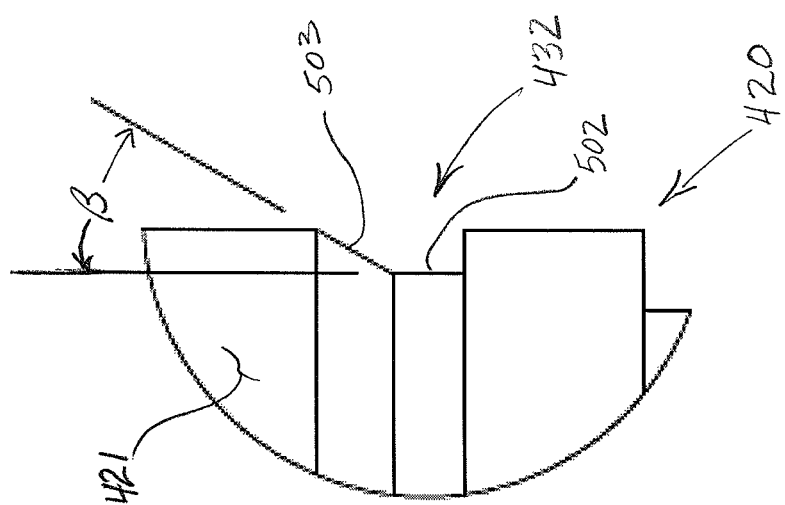
FIG. 5 is an enlarged detail view of a portion of a plunger shaft, according to some embodiments.

According to some embodiments, the engaging feature of plunger shaft 420 may be formed to further facilitate the disengagement of the mating feature of plunger 320 therefrom, for example, in those instances where plunger 320 may have taken a set within second length L2 of syringe 301, over the course of the above-described operation, so that expandable-contractible portion 33 of wiper sidewall 330 does not readily expand when terminal portion 421 of shaft 420 is moved into first length L1 of syringe. With reference to FIG. 5, which is an enlarged detail view of a portion of a plunger shaft 420, the engaging feature, or groove 432 of shaft 420 includes a beveled edge, or a distal chamfered shoulder 503, which can act to force the mating feature, or tabs 332 of plunger 320 radially outward, and out of engagement with groove 432, when plunger shaft 420 is retracted back into first length L1. FIG. 5 illustrates shoulder 503 extending distally from a base 502 of groove 432 at an acute angle β, for example, being between approximately 30° and approximately 75°, preferably approximately 30°, with respect to a longitudinal axis of plunger shaft 420.

Alternately, or in addition, a suction force may be created within syringe 301, by moving shaft 420, and thus, plunger 320 toward proximal opening 31, to facilitate the disengagement of plunger 320 from shaft 420. This suction force may cause the disengaged plunger 320 to be pulled within syringe 301, for example, toward first and second distal ports 300, 302. This action will disable subassembly 350 and prevent re-use thereof, since tabs 332 of expandable-contractible portion 33 will not allow shaft 420 to re-engage with plunger 320, when plunger 320 is within second length L2 of syringe 301. Additionally, retention of the disengaged plunger 320 within syringe 301 may provide for a sealing engagement thereof, with inner surface 311 of syringe 301, that prevents any fluid, that remains within syringe 301, from leaking out from proximal opening 31, for example, as subassembly 350 is being removed from a pressurizing unit. It should be noted that gap G between end wall 340 of plunger 320 and distal terminal end 440 of plunger shaft 420 (FIGS. 4A-B) may further facilitate the separation of plunger 320 from shaft 420, particularly in combination with the aforementioned suction force.

Figure 6A:
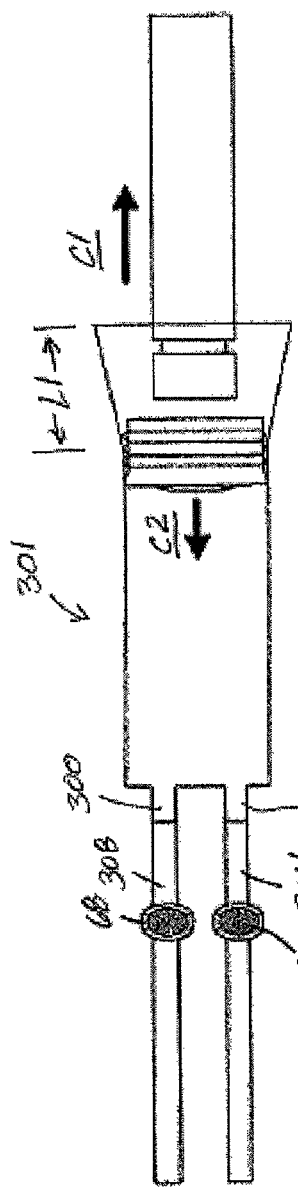
FIGS. 6A-C are schematics outlining some methods of the present invention.
Figure 6B:
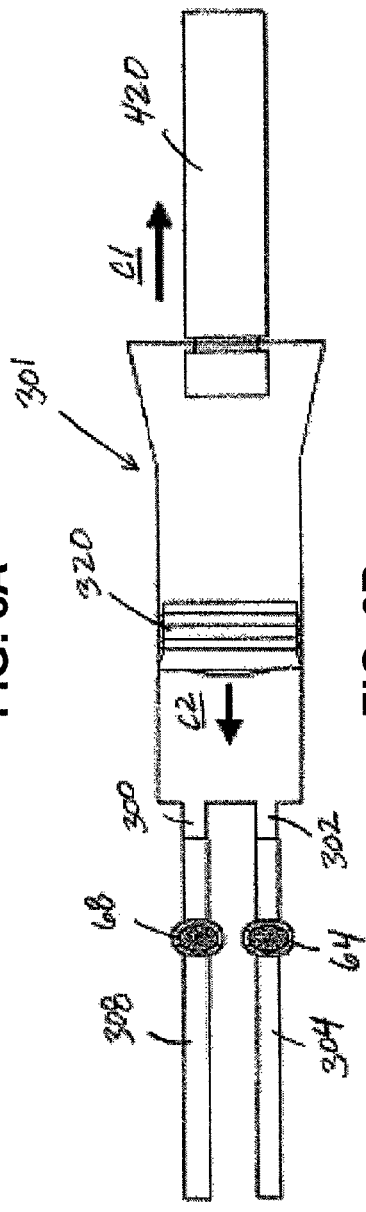
Figure 6C:
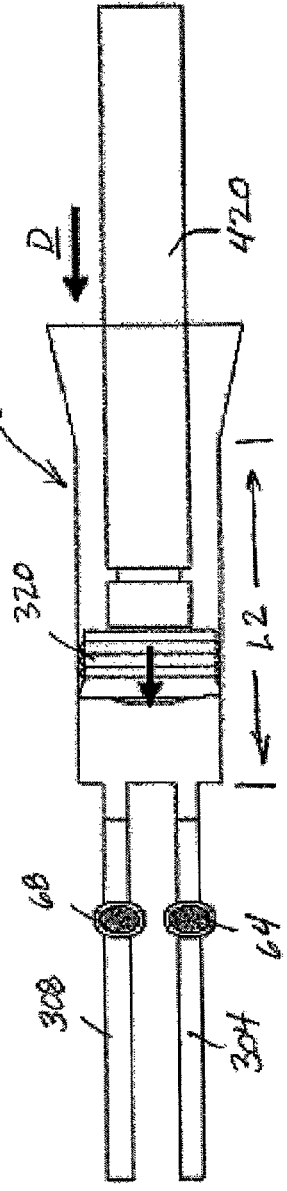

Turning now to the schematics of FIGS. 6A-C, some methods, which incorporate the aforementioned suction force for disabling and removing subassembly 350 from a pressurizing unit, will be described. The removal is typically performed at the end of a day of system operation, but may be performed more frequently. FIGS. 6A-C schematically illustrate a valve 68 coupled inline with inlet tubing line 308, and a valve 64 coupled inline with outlet tubing line 304; it should be understood that both valves 68, 64, for example, pinch valves, are typically closed upon completion of system operation for the day. According to preferred embodiments, the aforementioned controller, of each of injection systems 100, 200, may be pre-programmed to actuate both plunger shaft 420 and valves 64, 68 in order to carry out any of the methods described below.

FIG. 6A illustrates a method, in which both valves 68, 64 are closed, to isolate syringe 301 from downstream flow paths of fluid inlet and outlet lines 308, 304, so that a vacuum is created within syringe 301, as plunger shaft 420 moves plunger 320 proximally, per arrow C1, for example, at a speed between approximately 5 mm/sec and approximately 8 mm/sec. The vacuum, within syringe 301, creates a suction force, for example, between approximately 5 psi and approximately 20 psi, to pull plunger 320 distally, per arrow C2, and out of engagement with shaft 420. According to the illustrated embodiment, the disengagement occurs as plunger 320 is moved into first length L1 of syringe 301, being facilitated by the enlarged inner diameter thereof, but, according to alternate embodiments, this need not be the case. For example, the suction force created by the vacuum within syringe 301 may be sufficient, alone, to disengage plunger 320 from shaft 420, in which case syringe 301 may not include length L1 in which the inner diameter is enlarged to allow expansion of plunger 320, as previously described; or plunger 320 may not expand in length L1, either because plunger 320 has taken a set during the day's operation of the system or because plunger 320 does not include expandable-contractible portion 33. Alternately, the engaging feature of shaft 420 may be configured as illustrated in FIG. 5, to further facilitate disengagement of plunger 320 from shaft 420, via the suction force. According to some preferred methods, disengaged plunger 320 is allowed to be drawn back toward distal ports 300, 302 of syringe 301, for example, as shown in FIG. 6B, before syringe 301 and plunger 320, together, are separated from shaft 420 for removal of subassembly 350 from the pressurizing unit.

With further reference to FIG. 6B, the suction force, alone, may be sufficient to draw the disengaged plunger 320 toward distal ports 300, 302, for example, to both secure plunger 320 within syringe 301, for disposal of subassembly 350, and to wedge plunger 320 into sealing engagement with syringe, thereby preventing fluids from leaking out from proximal opening 31 as subassembly 350 is removed from the pressurizing unit. However, with reference to FIG. 6C, according to alternate methods, once the disengaged plunger 320 is pulled into second length L2 of syringe, by the suction force, shaft 420 is moved distally, per arrow D, to nudge plunger 320 further distally, within syringe, without re-engaging therewith, prior to separating subassembly 350 from shaft 420. According to some methods, after plunger 320 is disengaged from plunger shaft 420, shaft 420 is fully withdrawn from syringe 301, prior to opening valves 68, 64 and removing subassembly 350 from the system.

In the foregoing detailed description, the invention has been described with reference to specific embodiments. However, it may be appreciated that various modifications and changes can be made without departing from the scope of the invention as set forth in the appended claims.

We claim:

1. A plunger for a fluid pressurizing unit of an injection system, the plunger comprising:
   a wiper sidewall extending between a distal end and a proximal end of the plunger, the wiper sidewall including an internal surface and an external surface;
   a cavity being defined by the internal surface of the wiper sidewall and having an opening located at the proximal end of the plunger;
   a plurality of longitudinally extending ribs formed in the internal surface of the wiper sidewall and spaced apart from one another about a circumference of the cavity, each of the plurality of ribs extending from the proximal end of the plunger toward the distal end of the plunger; and
   a tab formed on each of at least some of the plurality of ribs, each tab located in proximity to the proximal end of the plunger and projecting into the cavity.

2. The plunger of claim 1, wherein an entirety of the wiper sidewall is formed from a thermoplastic material.

3. The plunger of claim 2, wherein the thermoplastic material is selected from the group consisting of:
   polypropylene and polyethylene.

4. The plunger of claim 1, further comprising:
   a deformable distal end wall, from which the wiper sidewall extends; and
   wherein the wiper sidewall further includes an external sealing lip being located in proximity to the distal end wall.

5. The plunger of claim 4, wherein the deformable distal end wall and the wiper sidewall are integrally formed from a thermoplastic material.

6. The plunger of claim 5, wherein the thermoplastic material is selected from the group consisting of:
   polypropylene and polyethylene.

* * * * *